US00PP33973P3

(12) United States Plant Patent
Clark

(10) Patent No.: US PP33,973 P3
(45) Date of Patent: Mar. 1, 2022

(54) PEACH TREE NAMED 'A-858P'

(50) Latin Name: *Prunus persica*
Varietal Denomination: A-858P

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/873,100

(22) Filed: Jan. 30, 2020

(65) Prior Publication Data

US 2021/0243927 P1 Aug. 5, 2021

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463
See application file for complete search history.

(56) References Cited

U.S. PATENT DOCUMENTS

| | | | |
|---|---|---|---|
| PP86 | P | 2/1934 | Blackburn |
| PP15,159 | P3 | 9/2004 | Clark |
| PP17,742 | P3 | 5/2007 | Clark |
| PP22,464 | P3 | 1/2012 | Clark |

OTHER PUBLICATIONS

Saturn Peach, Raintree Nursery, downloaded from raintreenursery.com/products/Saturn-peach-semi-dwarf on Jul. 17, 2021.*
TangOs(R) Peaches, Specialty Produce, downloaded from specialtyproduce.com/produce/Tango_Peaches_15050.php on Jul. 17, 2021.*
TangOs(R)II Peaches, Rutgers Licensing and Technology: Agricultural Products, downloaded from http://agproducts.rutgers.edu/fruit-trees/tangos2-peach.html on Jul. 17, 2021.*
Clark, J.R., et al., "'White Diamond' and 'White Cloud' Peaches," Hort. Science (2011) 46(4):665-667.

* cited by examiner

*Primary Examiner* — Anne Marie Grunberg
(74) *Attorney, Agent, or Firm* — Quarles & Brady LLP

(57) ABSTRACT

Description and specification of a new and distinct cultivar of peach tree named 'A-858P' which originated from a hand-pollinated cross of 'White Diamond' (female, U.S. Plant Pat. No. 22,464) x A-609P (male, non-patented, unreleased genotype) is provided. This new peach tree can be distinguished by its mid-early ripening, peen-tao (flat) shape, medium fruit size, semi-freestone flesh adherence, attractive skin, good flavor, and high tree health suitable for home garden use.

3 Drawing Sheets

Latin name: *Prunus persica.*
Varietal denomination: 'A-858P'.

BACKGROUND

A new and distinct peach tree called 'A-858P' is described herein. The new cultivar originated from a hand-pollinated cross of 'White Diamond' (female, U.S. Plant Pat. No. 22,464) and A-609P (male, non-patented, unreleased genotype) made in 2008. The seeds resulting from this controlled hybridization were germinated and grown in a greenhouse during the winter of 2008-2009 and were planted in an orchard near Clarksville, Ark. The seedlings fruited in the summer of 2012 and one was selected for its mid-early ripening, peen-tao (flat) shape, medium fruit size, semi-freestone flesh adherence, attractive skin, good flavor, and high tree health suitable for home garden use.

SUMMARY OF THE INVENTION

The new and distinct cultivar of peach tree originated from a hand-pollinated cross of 'White Diamond' (female, U.S. Plant Pat. No. 22,464) x A-609P (male, non-patented, unreleased genotype) made in 2008 near Clarksville, Ark.

The seeds resulting from this controlled hybridization were germinated in a greenhouse during the winter of 2008-2009. Resulting seedlings were planted in the spring of 2009 in an orchard near Clarksville, Ark. The seedlings fruited in the summer of 2012 and one seedling, designated Arkansas (A) 858P, and was selected for its medium fruit size, unique fruit shape, semi-freestone flesh adherence, attractive skin, good flavor, and high tree health. During 2009, the original plant selection was propagated asexually, at the above-mentioned location, by budding onto standard peach rootstock variety Guardian® BY520-9 (not patented) and a test plot of two plants was established.

The new variety has been asexually multiplied since 2009 at this location by budding onto Guardian® BY520-9 peach rootstock, and no incompatibility with peach rootstocks has occurred following budding. During all asexual multiplication, the characteristics of the original plant have been maintained and no aberrant phenotypes has appeared.

The new cultivar has been named the 'A-858P' cultivar.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'A-858P'

Figure 1A:
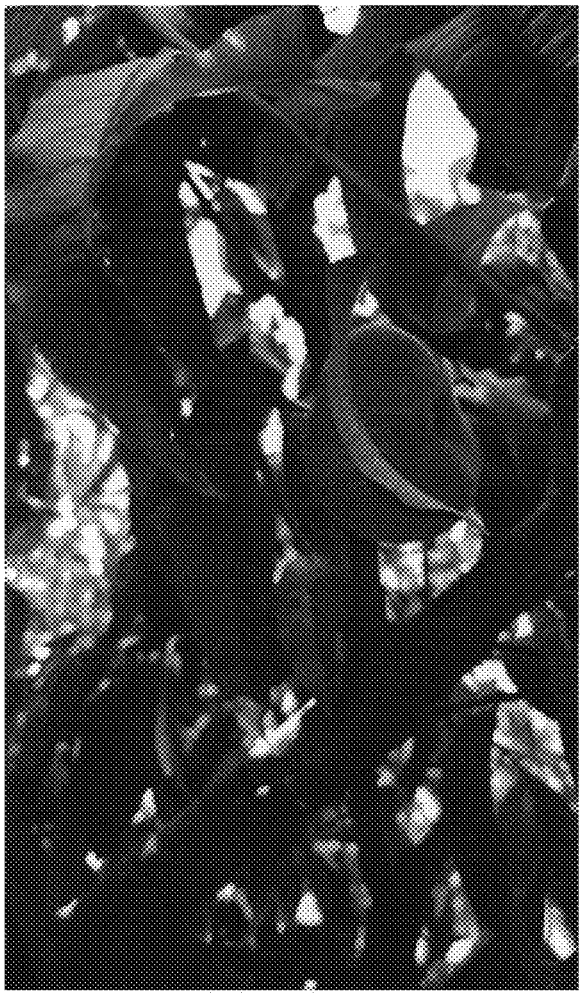
FIG. 1A and FIG. 1B show photographs of mature fruit on a tree of 'A-858P'.
Figure 1B:
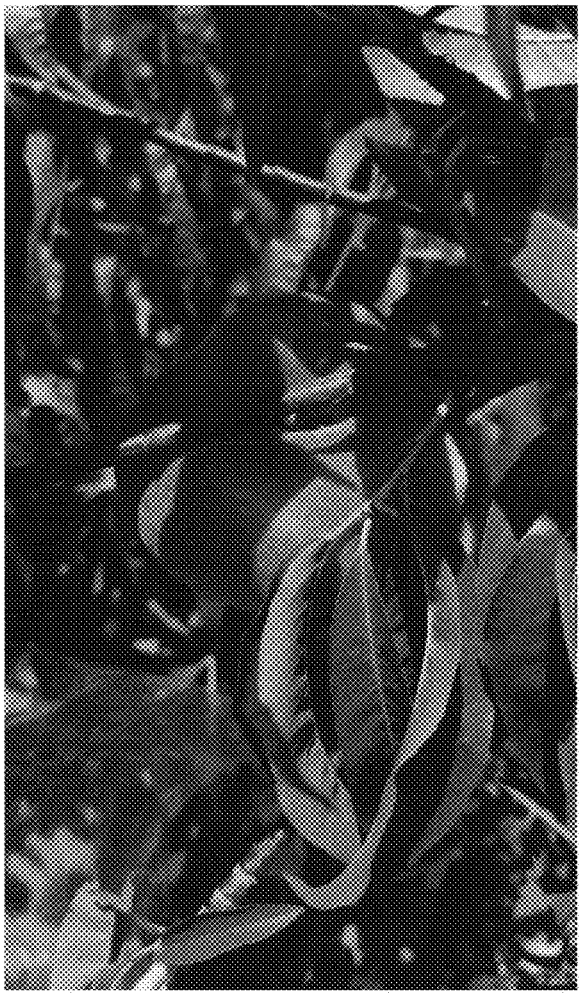
Figure 2:
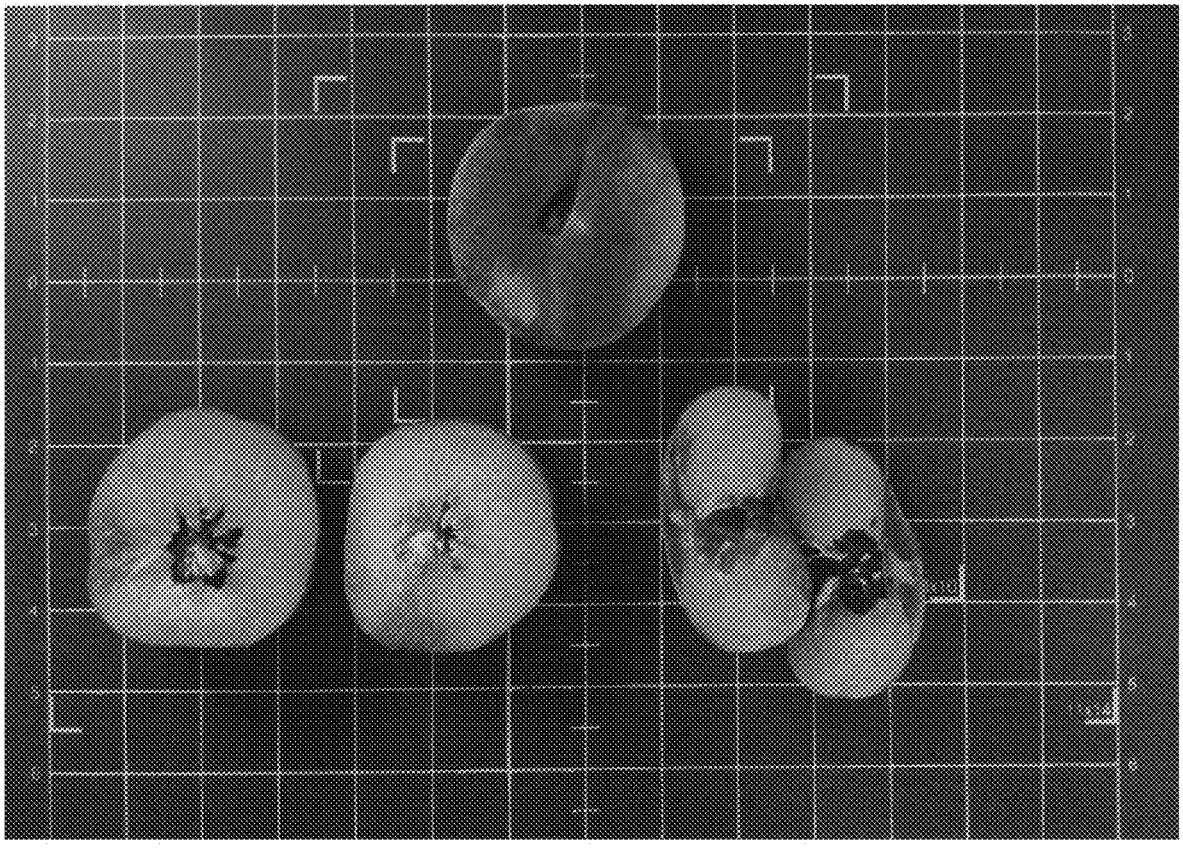
FIG. 2 is a photograph of whole, longitudinally cut, and latitudinally cut fruit of 'A-858P' at maturity.
Figure 3:
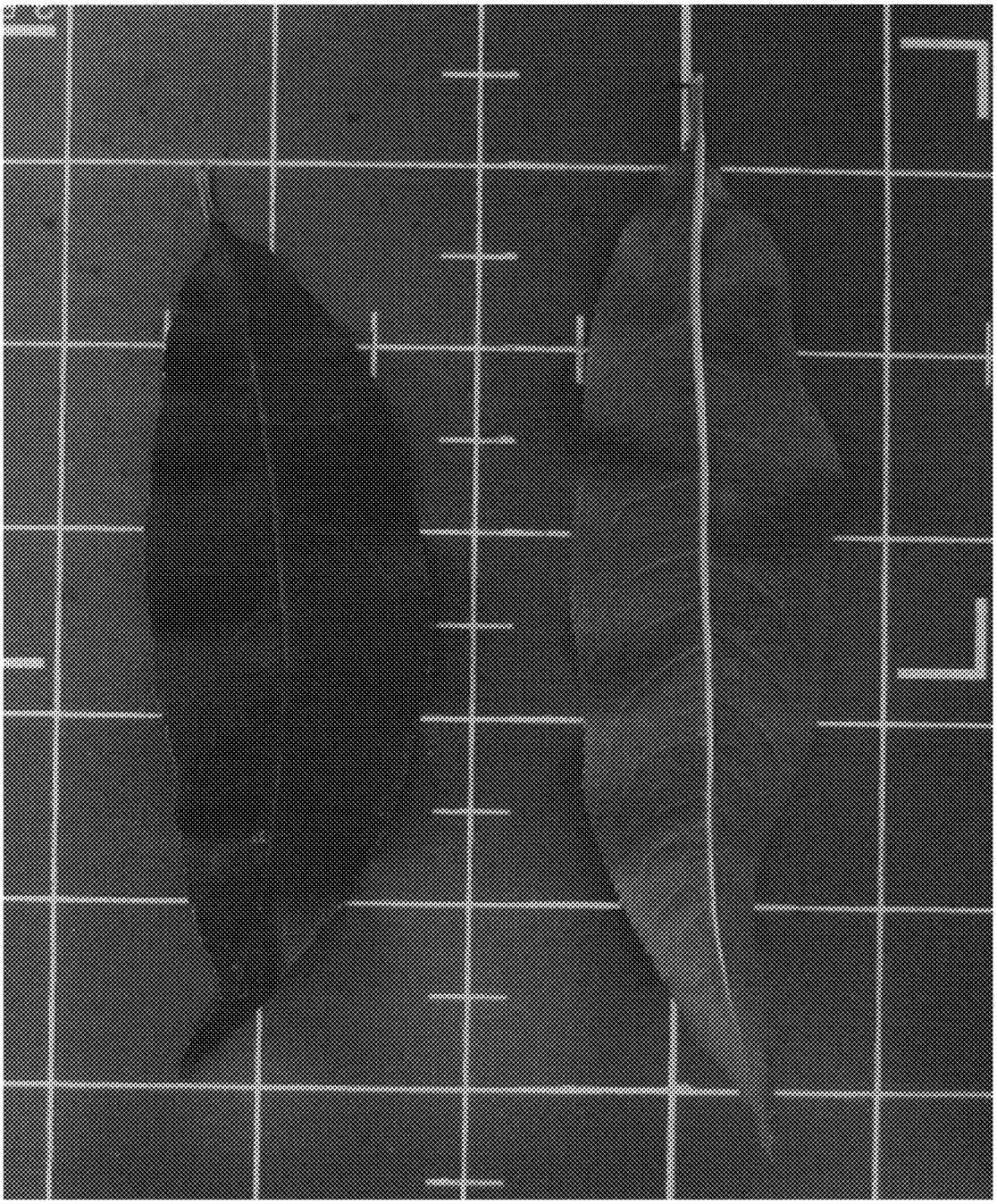
FIG. 3 is a photograph of mature 'A-858P' leaves, showing the adaxial (left) and abaxial (right) surfaces.

Plants and fruit of this new cultivar differ phenotypically from its parents. The new cultivar differs from parent 'White Diamond' in that it is peen-tao (flat-shaped) with yellow, melting flesh. In contrast, 'White Diamond', is a late-ripening, round, melting flesh type, low acid peach. The new cultivar also differs from its male parent, A-609P, as this parent is very early ripening and has white flesh and high acid flavor. The new cultivar has medium fruit (ave. 120 g) with attractive, high-blush skin, semi-freestone flesh adherence, sweet, good flavor, and high tree health. Some distal-end splitting of fruits was observed in evaluations. Both the parents and the new cultivar are the genus and species *Prunus persica* (L.) Batsch.

Plants of the new cultivar are vigorous and moderately productive, and trees are standard in size, well-branched, and symmetrical with an upright to semi-spreading growth habit, comparable to other peach trees (*Prunus persica*). Trees express a moderate level of resistance to both foliar and fruit infection of bacterial spot [*Xanthomonas campestris* pv. *pruni* (Smith) Dye], but in some years does not show complete immunity to this disease. Chilling requirement to break bud dormancy is estimated to be 800 hours below 45° F. (7° C.).

Fruit of 'A-858P' ripens mid-early season, averaging 27 June, with 'Stark® Saturn' (U.S. Plant Pat. No. 5,123), 'TangOs®' (U.S. Plant Pat. No. 18,997), and 'TangOs® II' (U.S. Plant Pat. No. 19,383). Fruit are peen-tao or flat-shaped, similar to 'Stark® Saturn', 'TangOs®', and 'TangOs® II'. Fruit of 'A-858P' are attractive with an average 90% red blush in contrast to 'TangOs®' and 'TangOs® II' which completely lack blush and are cream to green in color when fully ripe. Flesh of 'A-858P' is melting, similar to 'TangOs® II', and in contrast with the flesh of 'TangOs®', which has non-melting flesh. The flesh Flesh color of 'A-858P' is yellow-orange, unlike 'TangOs®', and 'TangOs® II' which have white flesh. Flesh adherence to the stone varies from semi-cling to freestone when fully ripe, in contrast with 'TangOs®' and 'TangOs® II' which are both clingstone. Fruit soluble solids content averaged 15.9%, sweeter than 'Stark® Saturn' which averages 13.3%. Trees indicated reliable fruiting and crop load was usually good.

The following is a detailed description of the botanical and pomological characteristics of the subject peach plant. Color data are presented in Royal Horticultural Society Colour Chart designations (1986 2$^{nd}$ edition). Where dimensions, sizes, colors and other characteristics are given, it is to be understood that such characteristics are approximations of averages set forth as accurately as achievable.

Plants used for botanical data were four years old and grown on a fine sandy loam soil with trickle irrigation near Clarksville, Ark. Trees were trained to an open-center system and dormant pruned annually. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were applied to the trees, but no bactericides were applied. The descriptions reported herein are from specimens grown near Clarksville, Ark.

Plant:

*Size*.—Mature trees (four years of age) average 3.0 to 3.5 m in height and 4.0 to 5.0 m in spread or width, and a semi-upright growth habit, as grown on Guardian® BY520-9 rootstock using an open center training system.

*Growth*.—Moderate vigor with good canopy development.

*Productivity*.—Moderately productive in observations but yield data not collected on trees. Tree is annual bearing; fruit is produced on long shoots.

*Cold hardiness*.—Wood and dormant buds hardy to 2° F. (−17° C.). This was the coldest temperature that the trees were exposed to at the test site, but hardiness may exceed this temperature.

*Disease resistance*.—Leaves and fruit are resistant but not immune to bacterial spot under growing conditions where bacterial spot infection is often very severe on susceptible genotypes. No bactericides were used in the development or evaluation of the instant cultivar. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Clarksville, Ark., was determined.

*Insect resistance*.—Insecticides were applied to orchards used in the development of the new cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (Synathedon pictipes (Grote & Robinson)), and greater peach tree borer (*Synanthedon exitiosa* (Say)). Therefore, no insect resistance was determined in the testing of the new cultivar.

Foliage/shoots/branches:

*Shoots*.—Smooth. Dormant-season (one-year-old) shoot (branch): length 140.5 cm; diameter at base 0.6 cm; diameter at midpoint 0.5 cm; diameter at terminal 0.3 cm. Dormant-season shoot color: Greyed Purple Group (187B). Color of apex: Greyed-Purple Group (187A) with bud scale outlines that are Brown Group (200B).

*Spur length*.—1.63 cm.

*Vegetative bud*.—Length: 0.04 cm; width: 0.02 cm; shape of apex: acute; color of apex: Greyed-White Group (156B); position in relation to one-year-old shoot: slightly held out; size of vegetative support shelf: length: 0.05 cm; width: 0.03 cm.

*Leaves*.—Simple, alternate, glabrous, lanceolate, petiolate, and deciduous. Venation pinnate; base acute; terminal or apex acuminate; margin serrated. Mature leaf size: length 11.9 cm; width midpoint 3.1 cm. Leaf serrations 5.6/cm. Mature leaf color: abaxial — Green Group (137C); adaxial — Green Group (137A). Young leaf color: abaxial — Yellow Green Group (146C); adaxial — Yellow Green Group (144A); and anthocyanin not present on abaxial or adaxial side of young leaves on midrib or other location. Petiole length — mature leaf: 1.1 cm. Petiole texture: smooth. Nectaries: reniform, average of 2 per leaf, located at the base of leaf blade nearest the distal portion of the petiole. Size of nectaries: width: 0.09 cm; length: 0.06 cm. Mature leaf petiole color: abaxial — Green Group (139D); adaxial — Green Group (139D). Stipule length: 2.1 mm; width: 0.5 mm. Stipule texture: smooth on both sides. Stipule color: abaxial — Yellow Green Group (144B); adaxial — tip: Greyed Purple Group (185A), base: Yellow Green Group (144B); shape in cross-section: v-shaped; length of blade tip: 5.27 mm.

*Buds*.—Number of leaf buds per 15 cm: 6.4, evenly distributed along the shoot. Number of flower buds per 15 cm from terminal: 14. Mature shoot internode length: base 2.5 cm, midpoint 2.5 cm, terminal 1.4 cm.

Bark (of mature trunk of tree):

*Color*.—Outer bark color: Greyed-Green Group (198C).

*Texture*.—Rough.

*Shoot and trunk lenticels*.—Color: Greyed-Orange Group (163B); density: 2 per $cm^2$.

Trunk:

*Diameter*.—11.3 cm (at 25 cm above ground level).

Flowers: Bloom occurs prior to vegetative bud break; solitary to occasional double individual flowers at a single node; perfect; self-fertile.

*Date of bloom*.—First, Julian 74 (March 14); Full, Julian 79 (March 19).

*Size*.—Diameter fully open 3.1 cm.

*Type*.—Showy.

*Flower*.—Shape: stellate; number per shoot: 21; flowers per stem: 1; depth 16.8 mm.

*Petals*.—Number of petals per flower: 5; length: 18.2 mm; width: 15.9 mm; texture: smooth on both abaxial and adaxial surfaces; shape: overall — obovate; apex: rounded; margin: smooth-entire; base: cuneate. Flower arrangement of the petals: touching to slightly overlapping. Minimal cupping of the petals is observed in fully open blooms.

*Color*.—Abaxial center: Red Group (54B), abaxial tips: Red Group (55D); adaxial center: Red Group (56A), tips: Red Group (56D).

*Pistil*.—Length: 9.9 mm; color: Red Purple Group (69B).

*Stamens*.—Average 52 per flower with pollen present, fertile and abundant. Average stamen length: 8.9 mm; stigma stands just slightly above the stamens. Anthers are positioned above the petal margins in an upright manner.

*Pollen color*.—Greyed Orange Group (163A).

*Ovary*.—Smooth; Color: Yellow Orange Group (19D).

*Sepals*.—5 per flower; shape: overall: ovate; apex: rounded; base: truncate; texture: abaxial — low to moderate pubescence; adaxial — low to no pubescence.

Fruit:

*Size*.—Medium for peen-tao peach fruit, avg. 120 g; diameter at stem end 6.0 cm, equator 7.2 cm, blossom end 6.3 cm; length base to apex 3.5 cm.

*Shape*.—Peen-tao, saucer-shaped; symmetry: moderately asymmetric; shape of fruit: base: depressed; apex: depressed; mucron tip; absent; depth of fruit stalk cavity: 6.79 mm; width of fruit stalk cavity: 15.19 mm; depth of fruit suture: 2.64 mm.

*Firmness*.—Medium to soft, typical of melting-flesh peaches.

*Skin*.—Texture: pubescence present and moderate to heavy (peach); attractive; ground color Yellow Orange Group (22B) with blush color Red Group (46A). Skin distal-end splitting observed on some fruits. Blush %: 90%, nearly solid coverage, slightly mottled; bloom on fruit skin: absent; lenticels are not present on fruit skin.

*Flesh*.—Color overall: Orange Group (24A); color nearest the skin: Orange Group (24A); color nearest the stone: Yellow Group (9C); semi-clingstone; melting texture; fruit skin is tightly adhered to the flesh; amount of fiber in flesh: average.

*Pedicel length*.—0.3 cm.

*Pedicel diameter*.—0.3 cm.

*Ripe date*.—27 June. Harvest period: about 10 days.

*Tendency of pit to split*.—Non-split.

*Fruit juice content* (%).—24% of total mass.

*Soluble solids*.—15.9%; Sweetness: sweet.

*Fruit juice pH*.—4.88.

*Fruit juice titratable acidity*.—0.21% expressed as malic acid.

*Storage performance*.—This genotype was not evaluated for storage potential or postharvest handling.

*Eating quality*.—Very good, with melting texture and good sugar and acid balance.

Pit/stone:

*Size*.—Length 1.3 cm; diameter (midpoint) 2.2 cm; width of stalk-end: 2.4 cm.

*Shape*.—Lateral view: oblate; ventral view: circular; basal view: circular; symmetry in lateral view: slightly asymmetrical.

*Texture of lateral surfaces*.—Hammered.

*Color*.—Greyed Orange Group (165A).

Kernel:

*Shape*.—Oval.

*Color*.—Greyed Orange Group (165B).

*Bitter or sweet*.—Bitter.

Uses: Fresh consumption; not evaluated for drying or other uses.

The cultivar: The most distinctive features of the new variety are its mid-early ripening, peen-tao (flat) shape, medium fruit size, semi-freestone flesh adherence, attractive skin, good flavor, and high tree health suitable for home garden use.

I claim:

1. A new and distinct cultivar of peach tree named 'A-858P,' as described and illustrated herein.

* * * * *